(12) United States Patent
Ransbury et al.

(10) Patent No.: US 8,204,596 B2
(45) Date of Patent: Jun. 19, 2012

(54) ISOLATION CONNECTOR FOR AN INTRAVASCULAR IMPLANTABLE MEDICAL DEVICE

(75) Inventors: Terrance Ransbury, Chapel Hill, NC (US); Stephen Purcell, Carborro, NC (US)

(73) Assignee: Synecor LLC, Chapel Hill, NC (US)

( * ) Notice: Subject to any disclaimer, the term of this patent is extended or adjusted under 35 U.S.C. 154(b) by 581 days.

(21) Appl. No.: 12/263,240

(22) Filed: Oct. 31, 2008

(65) Prior Publication Data
US 2009/0118798 A1   May 7, 2009

Related U.S. Application Data

(60) Provisional application No. 60/984,210, filed on Oct. 31, 2007.

(51) Int. Cl.
*A61N 1/00* (2006.01)
(52) U.S. Cl. .......................................... 607/37
(58) Field of Classification Search .............. 607/36, 607/37; 439/208, 342, 909
See application file for complete search history.

(56) References Cited

U.S. PATENT DOCUMENTS

| | | | |
|---|---|---|---|
| 4,678,868 A | 7/1987 | Kraska et al. | |
| 4,880,396 A * | 11/1989 | Lipari | 439/578 |
| 6,250,960 B1 * | 6/2001 | Youtsey | 439/578 |
| 6,920,673 B2 | 7/2005 | Allen et al. | |
| 7,082,336 B2 | 7/2006 | Ransbury et al. | |
| 7,254,443 B2 | 8/2007 | Jelen et al. | |
| 7,363,082 B2 | 4/2008 | Ransbury et al. | |
| 2004/0249431 A1 | 12/2004 | Ransbury et al. | |
| 2005/0043765 A1 | 2/2005 | Williams et al. | |
| 2006/0217779 A1 | 9/2006 | Ransbury et al. | |
| 2006/0247713 A1 | 11/2006 | Nicholson et al. | |
| 2008/0114413 A1 | 5/2008 | Fischbach et al. | |

* cited by examiner

*Primary Examiner* — Scott Getzow

(57) ABSTRACT

Devices and methods providing for a isolation connector for a generally cylindrical or frustro-cylindrical housing of an implantable intravascular medical device are described herein. The isolation connector has a generally annular exterior surface, a proximal end, and a distal end. The isolation connector includes a housing interface portion at the proximal end which is secured to a first end of the housing. The proximal end of the housing interface portion is constructed to be obverse to the first end of the housing and presents a perimeter of substantially similar size and shape to the perimeter of the first end of the housing. The isolation connector further includes a first insulator portion disposed adjacent to a distal end of the housing interface portion. The isolation connector may further include a feed-through channel constructed to traverse the proximal and distal ends of the isolation connector and is defined through the housing interface portion and the first insulator portion. In an optional embodiment, an electrical conductor is disposed within the feed-through channel to electrically coupled at least one component disposed within the housing to at least one component disposed beyond the insulator portion.

17 Claims, 18 Drawing Sheets

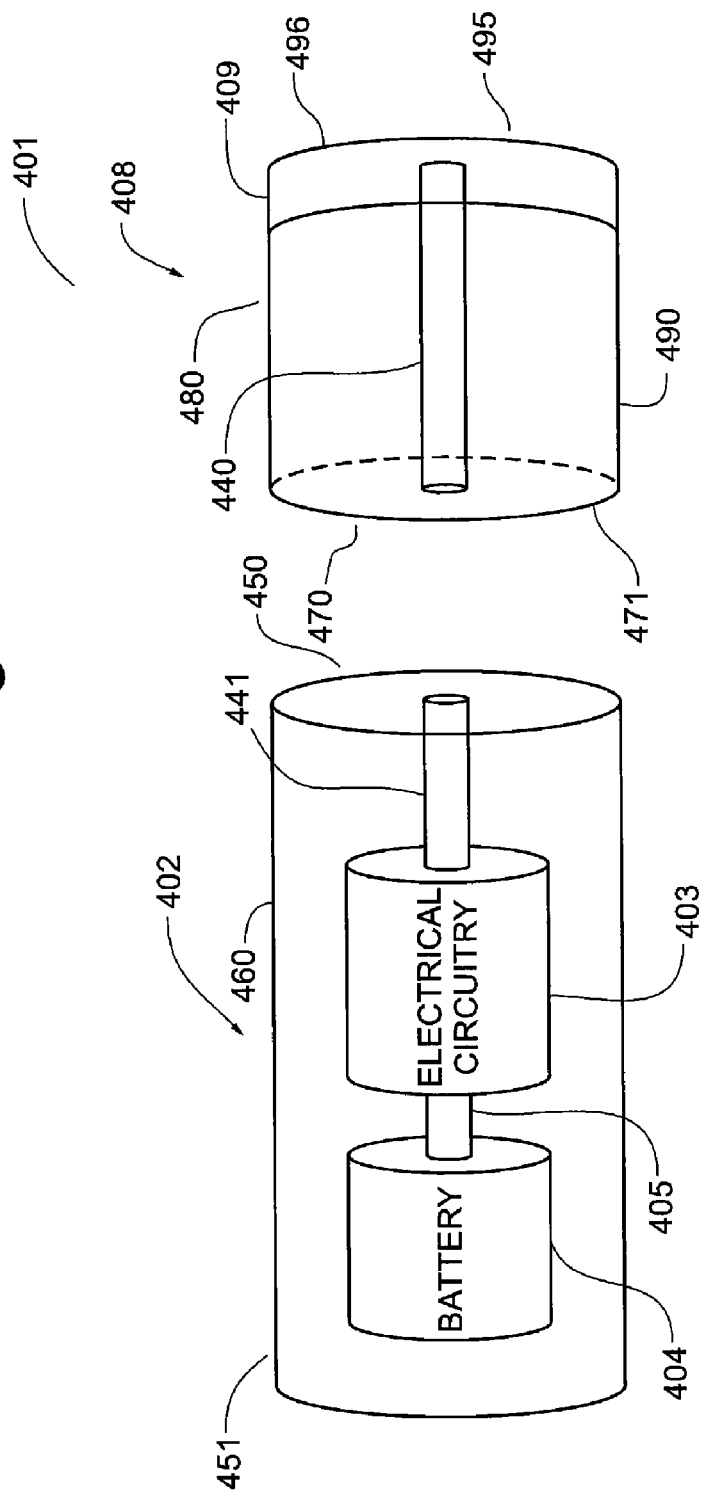

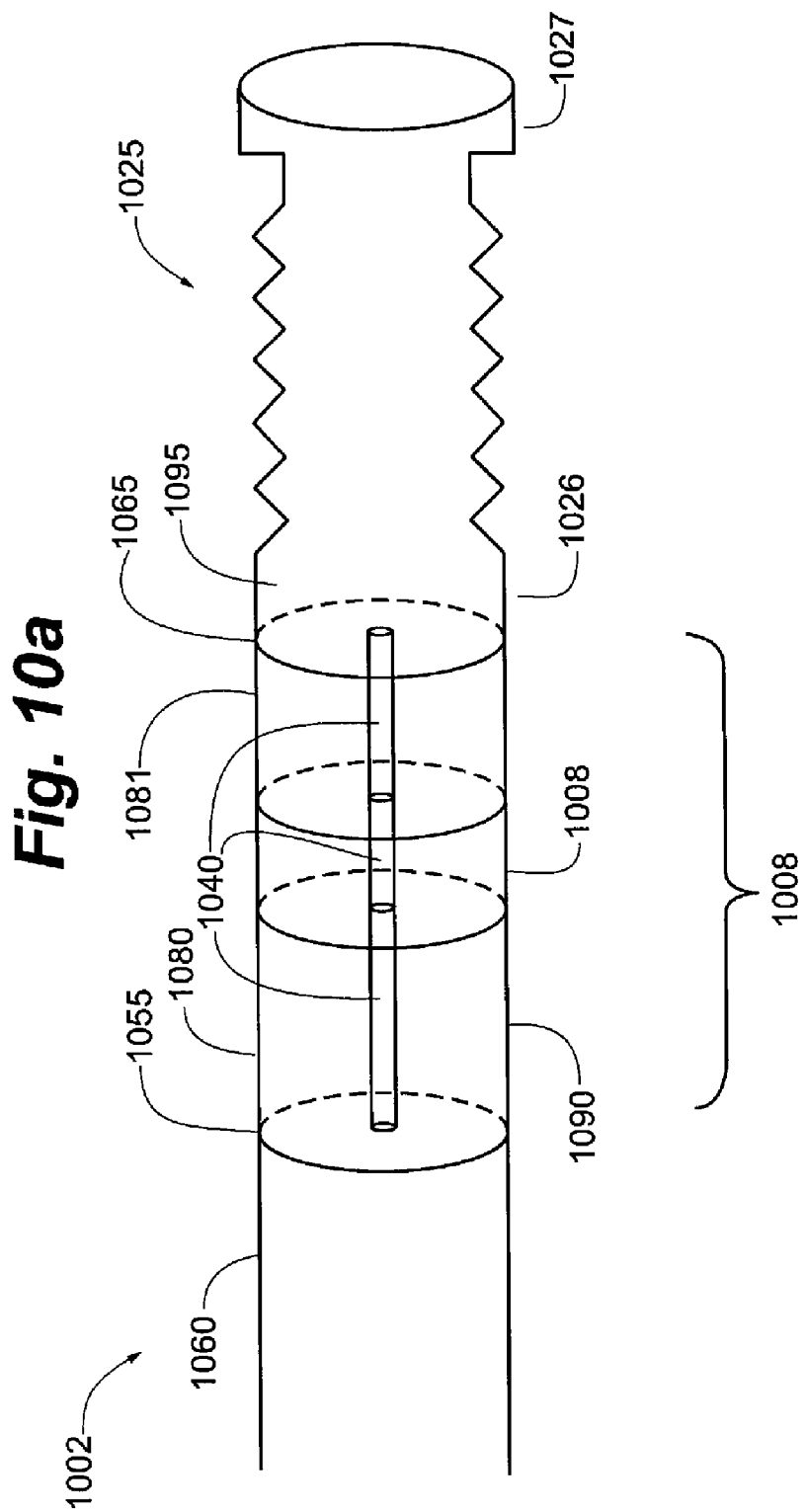

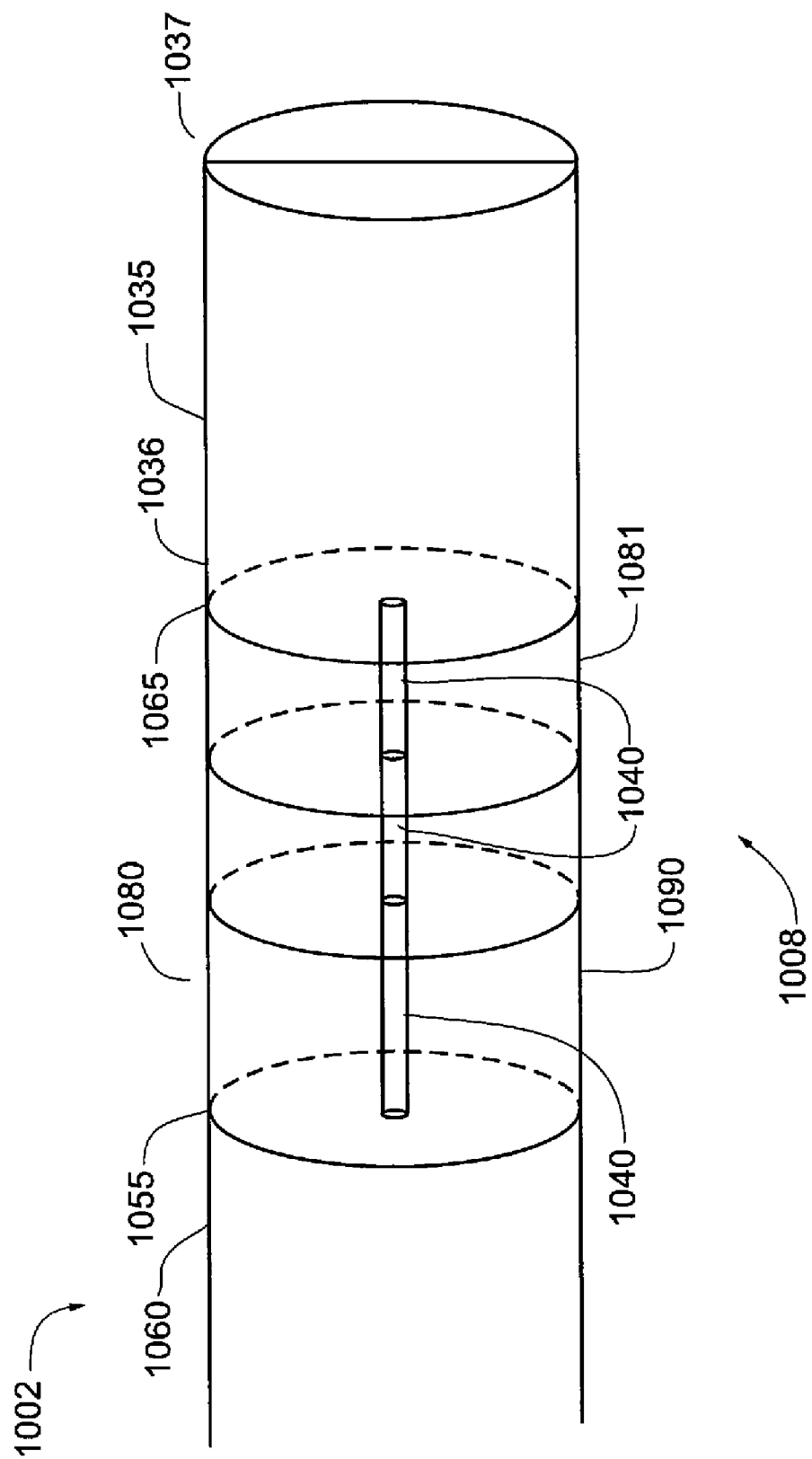

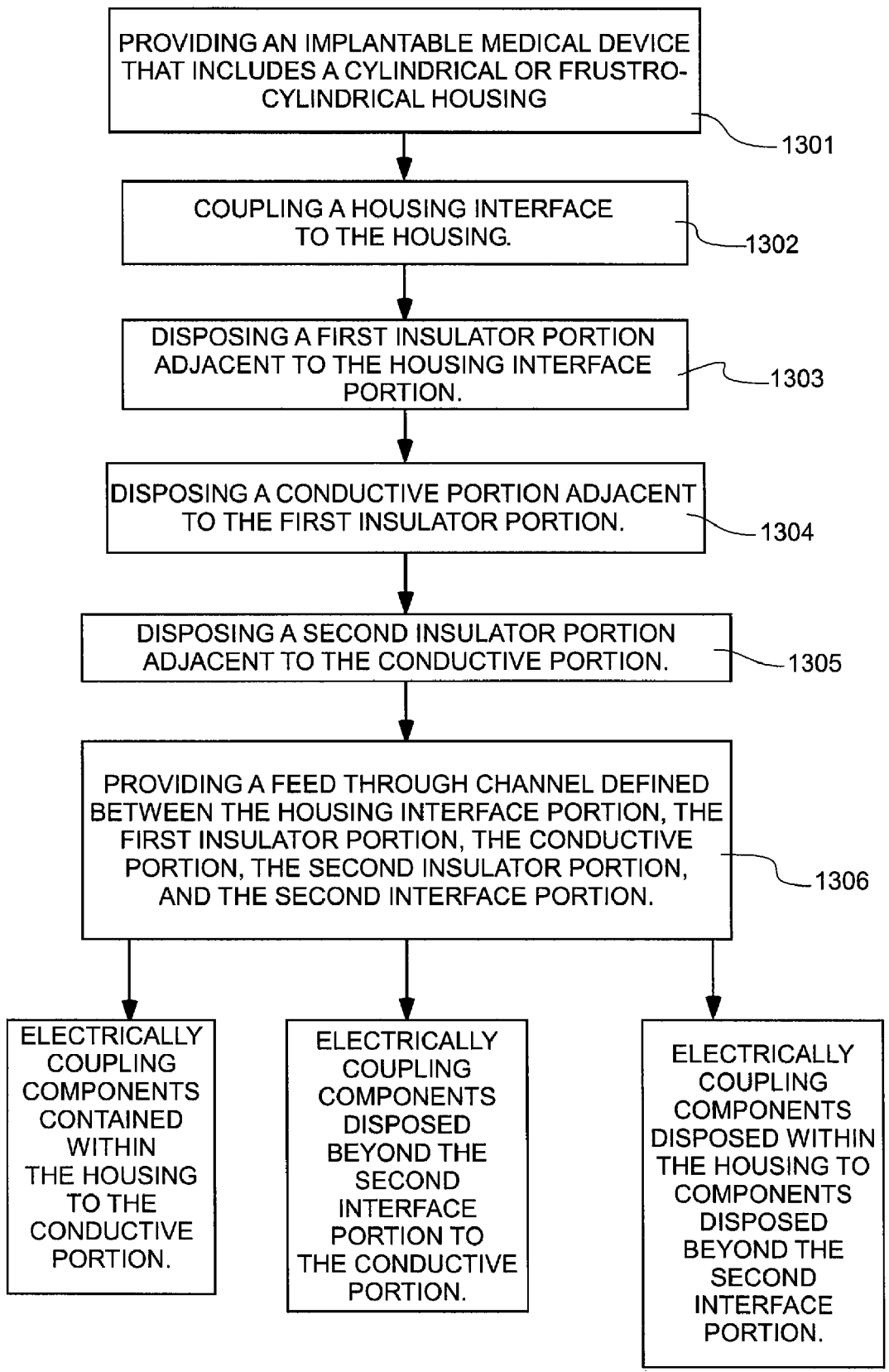

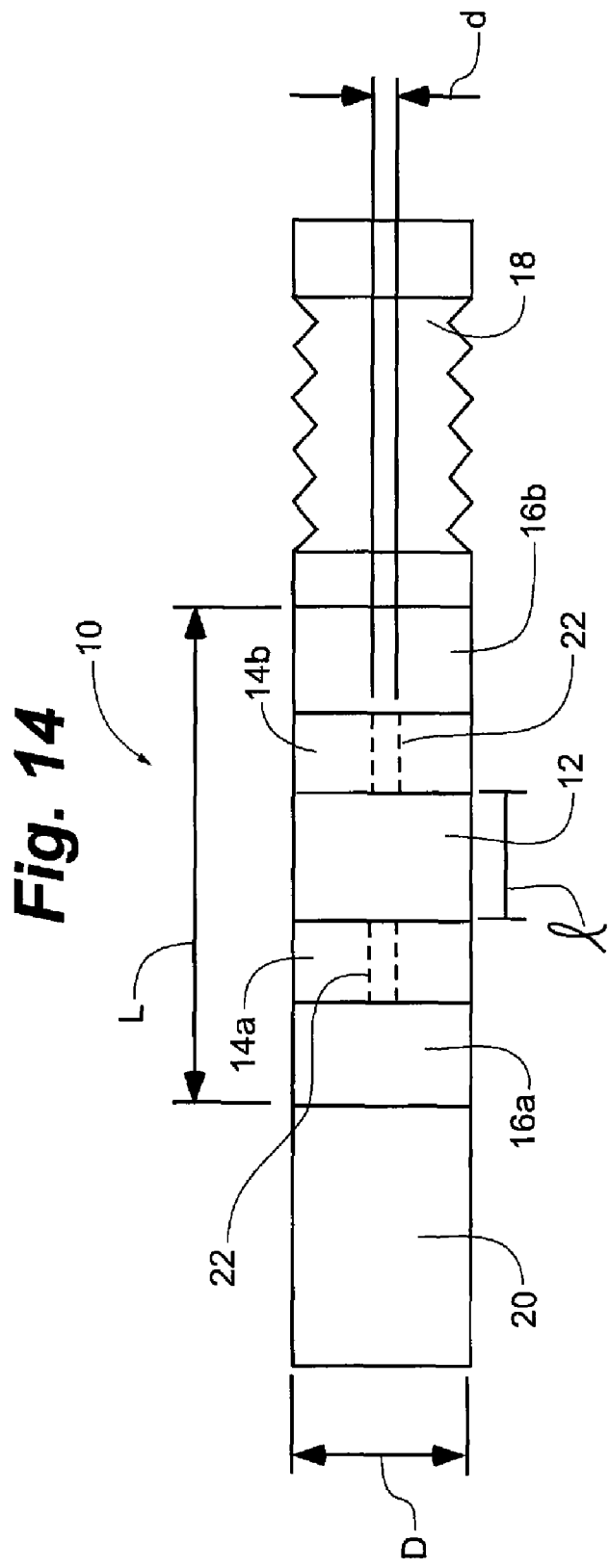

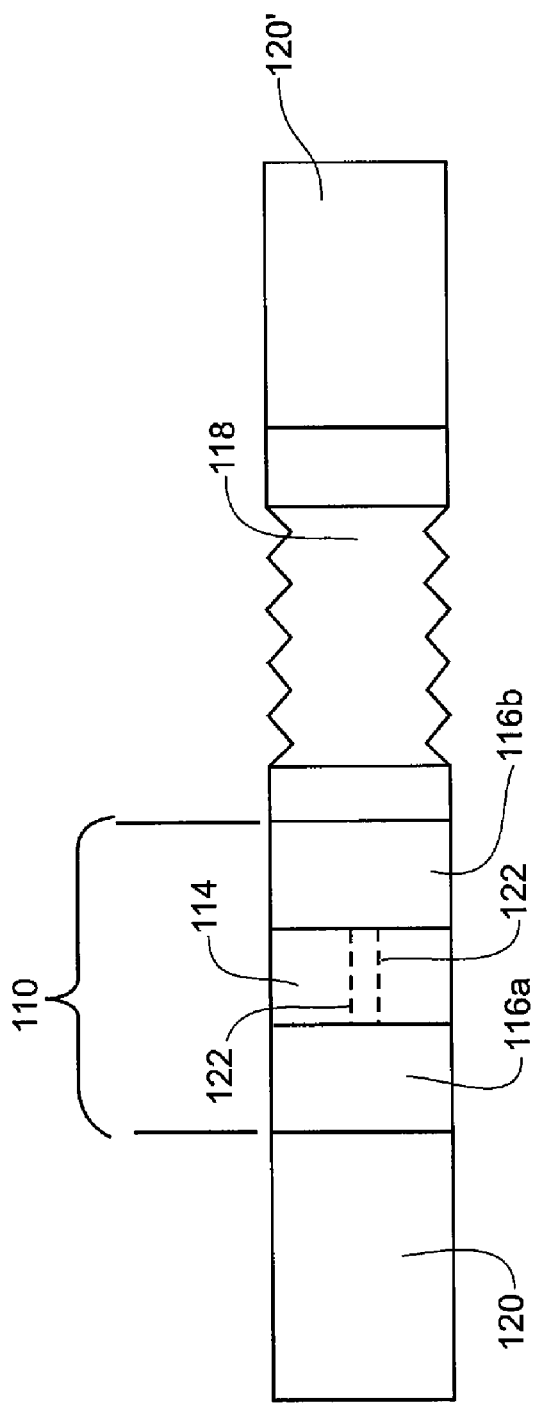

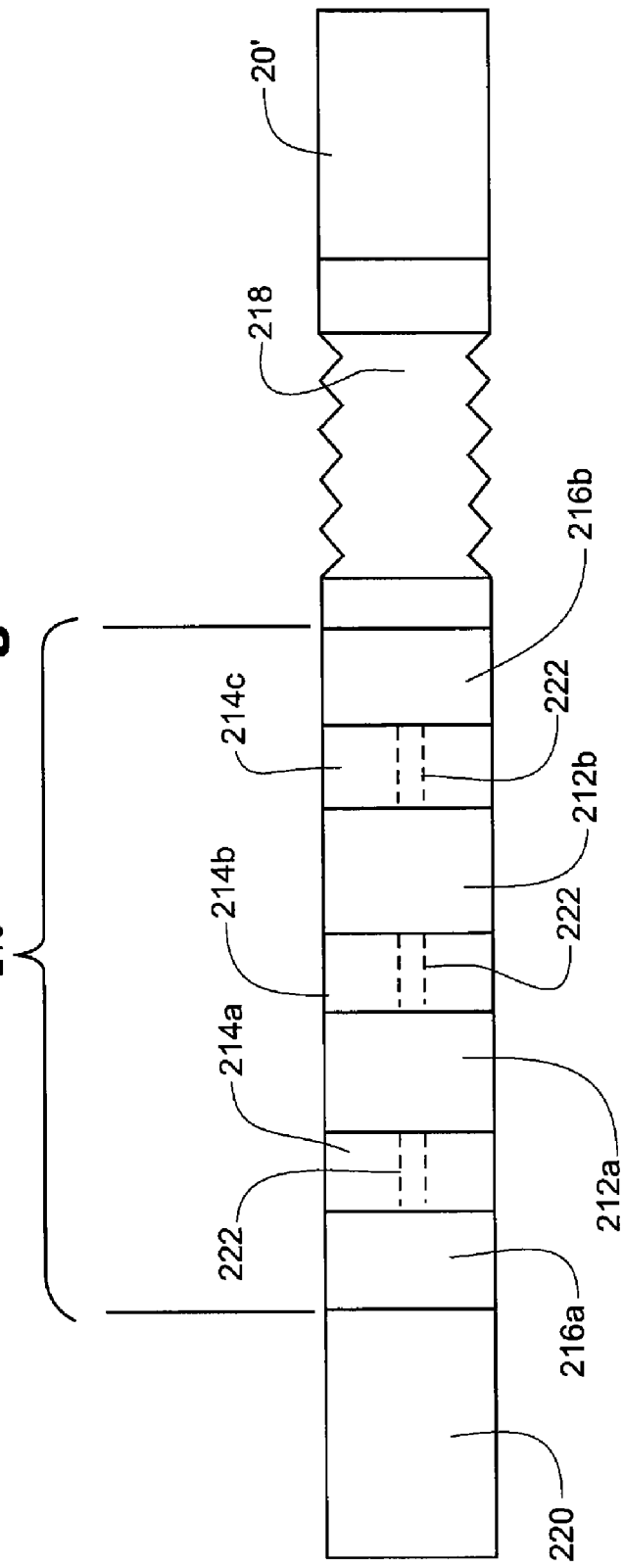

ISOLATION CONNECTOR FOR AN INTRAVASCULAR IMPLANTABLE MEDICAL DEVICE

RELATED APPLICATION

The present invention claims priority to U.S. Provisional Patent Application No. 60/984,210, entitled "Connector for Implantable Medical Device," filed Oct. 31, 2007 which is hereby incorporated by reference in its entirety.

FIELD OF THE INVENTION

The present disclosure relates generally to implantable medical devices. More particularly, the embodiments of the present disclosure relate to isolation connectors for connecting components in intravascular implantable medical devices.

BACKGROUND

An implantable medical device (IMD) is an apparatus that is typically placed inside a living body to monitor certain physiological signals and provide therapy to an organ or tissue. A typical IMD, such as a pacemaker, defibrillator or neurostimulator, is implanted subcutaneously in a convenient location beneath a patient's skin. Components of the IMD, such as electrical circuitry or batteries, are contained within a hermetically sealed housing. This housing is typically constructed to isolate IMD components from the human body. A typical IMD includes electrodes that are adapted to sense physiological conditions or to deliver therapy, for example the delivery of electrical energy to one or more portions of the heart of a patient. The IMD may include one or more electrical leads that couple one or more electrodes to electrical circuitry disposed within the IMD housing. An IMD may also include electrodes on the surface of the housing.

Leads are typically adapted to carry current from the IMD to the tissue to stimulate the tissue in one of several ways, again depending upon the particular therapy being delivered. Leads may also be used for sensing physiologic signals to determine when to deliver a therapeutic pulse to the tissue, and the nature of the pulse, e.g., a pacing pulse or a defibrillation shock. Alternatively, a catheter lead may be connected to an IMD to deliver drugs to various body parts for pain relief, defibrillation threshold reduction, and so forth.

Because IMDs are disposed within the human body, attention must be paid to interfaces between an IMD housing and leads or electrodes connected to IMD components disposed within the housing. These interfaces, also referred to as feed-through connectors, are typically constructed to ensure that the IMD functions properly and does not negatively interfere with bodily functions of a patient. For example, a feed-through connector may be adapted to prevent bodily fluids from entering a housing and interfering with the IMD components disposed within the housing. A feed-through connector may also isolate electrical currents carried by a lead or electrode from the IMD housing.

Many solutions have been proposed to connect electrical leads to an implantable medical device housing. For example, some feed-through connectors connect a lead to IMD components through an aperture formed in a portion of an exterior surface of the housing, such as disclosed in U.S. Pat. No. 4,678,868 to Kraska et al, U.S. Pat. No. 6,920,673 to Allen et al, and U.S. Pat. Pub. No. 2006/0247713 to Nicholson et al. These feed-through connectors typically extend perpendicularly outward from a portion of an exterior surface of the housing. These feed-through connectors also typically include an insulator that surrounds a portion of a lead in proximity to the housing in order to insulate the housing from the lead. Other IMD housings include a header or other hermetic extension of the housing to further isolate a feed-through connector, such as disclosed in U.S. Pat. Pub. No. 2008/0114413 to Fischbach et al. For IMD housings that include a header, a feed-through connection may be provided in a surface of the housing itself, or in a surface of the header. Still other IMD housings include a hermetic connector block extension that extends from an IMD housing header along a portion of the housing exterior, such as disclosed in U.S. Pat. No. 7,254,443 to Jelen et al.

Recently, elongated IMDs have recently been developed that are adapted to be implanted in the vasculature system of a patient instead of being implanted subcutaneously like conventional IMDs. These elongated intravascular implantable devices (IIDs) may take the form of a plurality of independent, substantially cylindrical or frustro-cylindrical housings, such as disclosed by U.S. Pat. No. 7,363,082 to Ransbury et al. These housings may be connected together through a series of flexible components such as bellows so that the elongated implantable medical device is flexible enough to be introduced to and disposed within the vasculature system of a patient.

Chronically implanting an IID within the vasculature system of a patient presents a number of problems that are significantly different than implanting a conventional subcutaneous IMD because the IID must be constantly exposed to the blood stream of a patient. In addition, the IID and leads or electrodes of an elongated IID must be sized, shaped, and arranged to be disposed entirely within the limited space and shape of an elongated vasculature organ, such as an artery or vein of the patient.

As such, existing feed-through connectors for IMDs are of limited for use with an elongated IID because typical IMD feed-through connectors are formed to protrude perpendicularly outward relative to an IMD housing surface or header. As a result, these IMD feed-through connectors are effectively limited only to the ends of a generally elongated cylindrical housing arrangement. If existing IMD feed-through connector were to be used at locations other than the ends of an IID housing arrangement, the feed-through connectors would present exposed protrusions that may interfere with blood flow within the vasculature organ or cause undesirable coagulation along one or more surfaces of the feed-through connector or housing. Therefore, a need exists for an improved isolation connector for an elongated intravascular implantable medical device.

SUMMARY OF THE INVENTION

An implantable intravascular medical device that includes a cylindrical or frustro-cylindrical housing and an isolation connector is described herein. The isolation connector has a generally annular exterior surface, a proximal end, and a distal end. The isolation connector includes a housing interface portion at the proximal end which is secured to a first end of the housing. The proximal end of the housing interface portion is constructed to be obverse to the first end of the housing and presents a perimeter of substantially similar size and shape to the perimeter of the first end of the housing. The isolation connector further includes a first insulator portion disposed adjacent to a distal end of the housing interface portion. In some embodiments, the isolation connector may further include a feed-through channel constructed to traverse the proximal and distal ends of the isolation connector and defined through the housing interface portion and the first insulator portion. In an optional embodiment, an electrical conductor is disposed within the feed-through channel to electrically coupled at least one component disposed within the housing to at least one component disposed beyond the insulator portion.

A cylindrical or frustro-cylindrical isolation connector for an implantable intravascular medical device that includes a cylindrical or frustro-cylindrical housing is also described herein. The isolation connector includes a proximal end that includes a housing interface portion constructed to present an interface with an end of a generally cylindrical or frustro-cylindrical implantable intravascular medical device housing that has a generally annular perimeter. The housing interface portion is adapted to be hermetically secured to the end of the housing. The housing interface portion includes a generally annular perimeter of similar size and shape to the generally annular perimeter of the housing. The isolation connector also includes a first insulator portion. The first insulator portion is disposed adjacent to a distal end of the housing interface portion. The isolation connector may further includes a feed-through channel defined through the housing interface portion and the first insulator portion and is constructed to traverse the proximal end and the distal end of the isolation connector. In an optional embodiment, the isolation connector further include an electrical conductor disposed within the feed-through channel such that at least one component disposed within the housing is electrically coupleable to at least one component disposed beyond the insulator portion via the electrical conductor.

A method of electrically coupling a first component of an intravascular implantable medical device disposed within a generally cylindrical or frustro-cylindrical housing of the medical device to a second component of the device not disposed within the housing is described herein. The method includes coupling a housing interface portion constructed to present an annular coupling end of substantially similar size and shape to at least one end of the housing. The method further includes coupling a first insulator portion to a distal end of the housing interface portion. The method also includes electrically coupling the first component of the intravascular implantable medical device to the second component of the device via an electrical conductor at least partially disposed within a feed-through channel defined through the housing interface portion and the insulator portion.

BRIEF DESCRIPTION OF THE FIGURES

The invention may be more completely understood in consideration of the following detailed description of various embodiments of the invention in connection with the accompanying drawings, in which:

FIG. 4 illustrates generally one embodiment of an IID including an isolation connector according to various aspects of the invention described herein.

FIGS. 10a and 10b illustrate generally embodiments of an isolation connector that include a second insulator portion and a second interface portion according to various aspects of the invention described herein.

FIG. 13 illustrates generally one embodiment of a method of providing an isolation connector for an implantable medical device housing according to various aspects of the invention described herein.

FIG. 14 illustrates generally a flattened perspective view of isolation connector according to various aspects of the invention described herein.

FIG. 15 illustrates generally a flattened perspective view of isolation connector according to various aspects of the invention described herein.

FIG. 16 illustrates generally a flattened perspective view of a isolation connector that includes first, second and third insulator portions according to various aspects of the invention described herein.

Figure 1:
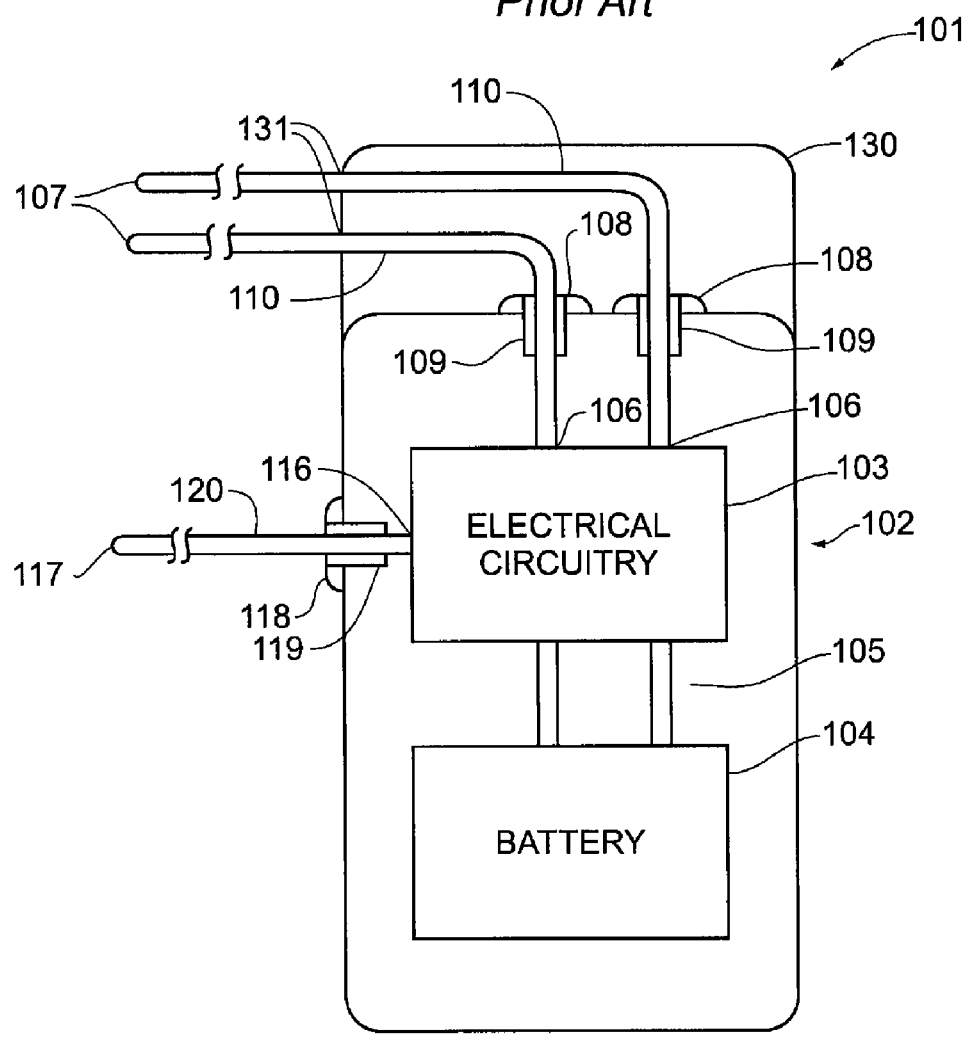
FIG. 1 illustrates generally one example of a typical prior art IMD.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE PREFERRED EMBODIMENTS

Figure 2:
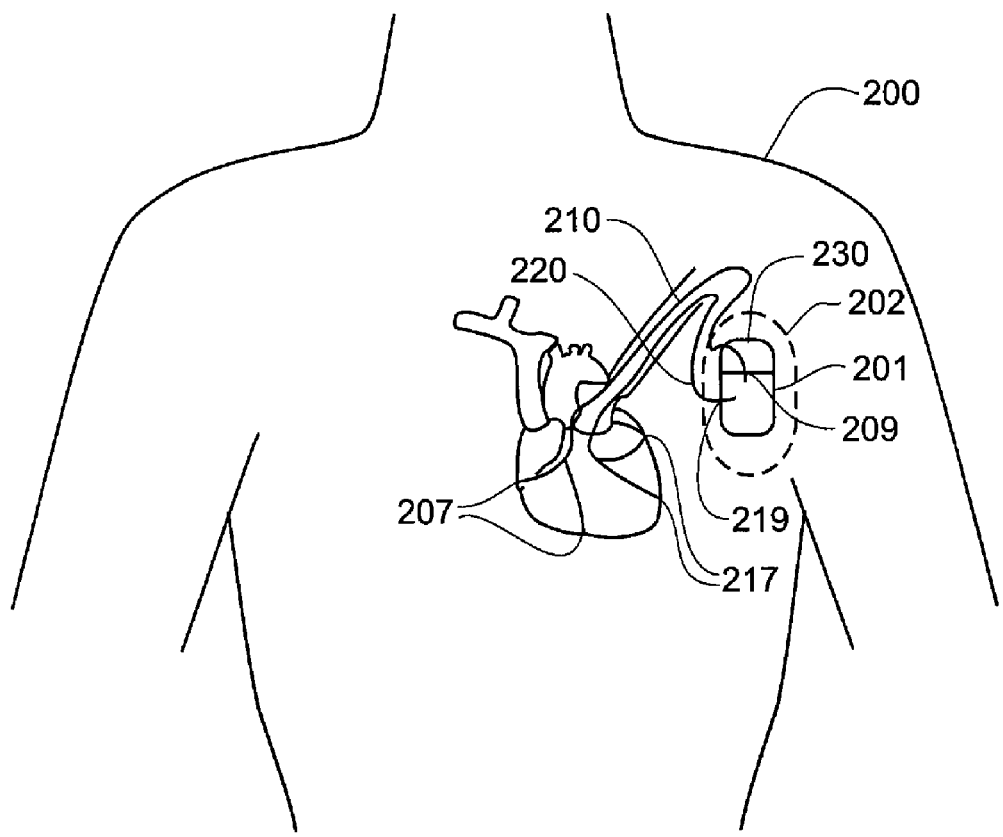
FIG. 2 illustrates generally one example of a prior art IMD housing disposed within the body of a patient.

FIGS. 1 and 2, and the below descriptions of FIGS. 1 and 2, are presented to explain the nature of typical prior art subcutaneous implantable medical devices (IMDs), such as pacemakers, defibrillators and neurostimulators. FIG. 1 illustrates generally one example of a typical IMD 101. IMD 101 includes components such as electrical circuitry 103 and battery 104 disposed within IMD housing 102. Electrical circuitry 103 may be coupled to battery 104 via electrical connectors 105.

IMD 101 further includes one or more leads 110, 120. Leads 110, 120 are adapted to couple electrical circuitry 103 and battery 104 to one or more electrodes 107, 117 disposed along, or at a distal end of, leads 110, 120. Electrodes 107 are adapted to sense hemodynamic conditions and deliver therapy, for example delivery of electrical energy to cardiac tissue.

Leads 110, 120 are connected to electrical circuitry 103 and battery 104 via feed-through connectors 108, 118. Feed-through connectors 108, 118 are an aperture in a planar exterior surface of housing 102 to allow connection of leads 110, 120 to IMD components 103, 104 disposed within housing 102. Feed-through connectors 108, 118 are typically adapted to hermetically seal an interface between lead 110, 120 and housing 102. Feed-through connectors 108, 118 may further include insulator portions 109 and 119. Insulator portions are constructed to electrically isolate lead 102 from housing 102.

Feed-through 118 as depicted in FIG. 1 is defined by an aperture in a planer exterior surface of housing 102. Lead 120, or another electrical conductor electrically coupled with lead 120, may be connected to electrical circuitry 103. Lead 120 extends through feed-through connector 118 to the exterior of housing 102. Outside housing 102, at least a proximal portion of lead 120 is arranged generally perpendicular to the exterior surface of housing 102

Feed-through 108 is also defined by an aperture in an exterior surface of housing 102, however housing 102 further includes header portion 130. Header portion is constructed to at least partially surround a proximal portion of leads 110. Header portion may include apertures 131, or may itself include feed-throughs. Feed-throughs 108 may be located on a surface of header 130 instead of at a surface of housing 102 as depicted in FIG. 1.

FIG. 2 illustrates generally one example of an IMD housing 201 disposed within the body of a patient. In the illustrated example, housing 201 is disposed within a cavity 202 beneath the skin in a chest region of patient 200. Leads 210, 220 electrically couple electrodes 207 to components held within housing 201 via feed-through connectors 209 219. Leads 210, 220 are introduced to the body of patient 200 through the patient's vasculature system. Electrodes 207, 217 disposed at a distal end or along leads 210 are placed in proximity to or in direct contact with cardiac tissue so that they may measure hemodynamic conditions or deliver therapy. Disposition of an IMD 201 beneath the skin of patient may be a complicated procedure, because a physician may have to make a relatively large incision.

Figure 3A:
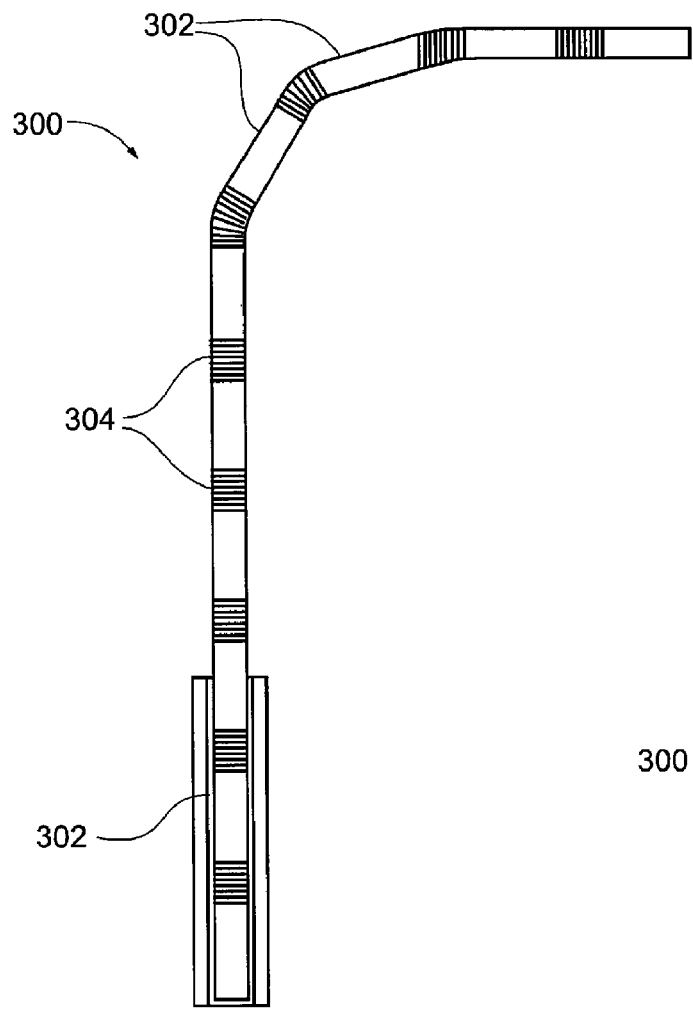
FIGS. 3a and 3b illustrate generally an example of an elongated IID adapted to be chronically implanted within the vasculature of a patient.
Figure 3B:
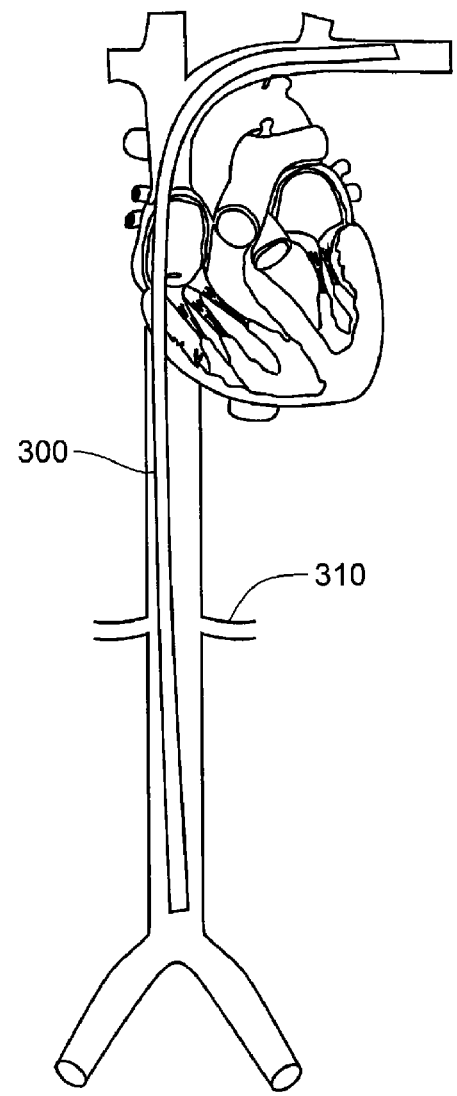

FIGS. 3A and 3B, and the below descriptions of FIGS. 3A and 3B, are presented to explain the nature of recent developments providing for implantable intravascular devices (IIDs) that may be chronically implanted in the vasculature of a patient. FIGS. 3A and 3B illustrate generally an example of an IID 300 adapted to be chronically disposed within a vasculature organ 310 of a patient 200. As illustrated in FIG. 3A, IID 300 includes a plurality of rigid or semi-rigid component housings 302. IID 300 may further include a plurality of bendable portions 304. Bendable portions 304 may be a bellows, as depicted, or any other readily bendable components. Housings 402 and bendable portions 404 may be arranged such that IID 300 may be introduced to and chronically disposed in a human vasculature organ 310 as depicted in FIG. 3B.

Further examples of IIDs adapted to be chronically disposed within the vasculature 310 of a patient 200 are described in U.S. Pat. No. 7,082,336, U.S. Patent Publication No. 2006/0217779, U.S. Patent Publication No. 2005/0043765, and U.S. Patent Publication No. 2004/0249431, all of which are incorporated by reference in their entirety. Incorporation by reference of these patents and published applications is limited such that no claims included in the patents and published applications are incorporated by reference herein. Also, any definitions provided in the patents and published applications are not incorporated by reference herein unless such definitions are expressly included herein.

FIG. 4 illustrates generally one embodiment of an IID 401 including a isolation connector 408 according to various aspects of the invention described herein. IID 401 includes components 403 and 404 contained within housing 402. In various embodiments, housing 402 is constructed to be a cylindrical or frustro-cylindrical shape. Housing 402 includes an annular outer surface 460, first end 450, and second end 451. In an embodiment, an outer perimeter of first end 450 may be defined by a cross-sectional dimension of annular outer surface 460. Housing 402 may further include electrical connector 441 to extend electrical connections of components 403, 404 towards the exterior of housing 402.

Also illustrated in FIG. 4 is one embodiment of an isolation connector 408. Like housing 402, isolation connector 408 may also be constructed to be a cylindrical or frustro-cylindrical shape. Isolation connector 408 may include an annular outer surface 490, a proximal end 470, and a distal end 495. Proximal end 470 and distal end 495 include annular perimeters 471 and 496, respectively.

Proximal end 470 may include housing interface portion 480. In various embodiments, housing interface portion 480 is constructed to be obverse to first end 450 of housing 402. In one such embodiment, an annular perimeter 471 of housing interface portion 480 is defined by a cross-sectional dimension of annular outer surface 490 of isolation connector 408. In some embodiments, annular perimeter 491 of housing interface portion 480 is of substantially similar size and shape to the annular perimeter 451 of first end 450 so as to provide a substantially flush interface between housing 402 and isolation connector 408 along annular outer surfaces 450 and 490. In an embodiment, the interface between housing 430 and isolation connector 408 is constructed to present a protrusion along outer surfaces 460 and 490 of less than 0.010 inches. In another embodiment, the interface between housing 430 and isolation connector 408 is constructed to present a protrusion along outer surfaces 460 and 490 of no greater than 0.0050 inches and optimally no greater than 0.0025 inches. In an alternative embodiment, annular perimeter 491 of housing interface portion 480 is not of substantially similar size and shape to the annular perimeter 451 of first end 450. According to this embodiment, annular perimeter 491 may have a greater diameter than annular perimeter 451, or annular perimeter 451 may have a greater diameter than annular perimeter 491. Also according to this embodiment, the annular perimeter with a greater dimension may be constructed to be generally arcuate in reference to an exterior surface of the adjacent component in order to reduce the sharpness of the interface between housing 430 and isolation connector 408.

In an embodiment, first end 450 of housing 402 and housing interface portion 480 may be coupled to one another via laser welding, brazing or any other means of hermetically coupling first end 450 of housing 402 to housing interface portion 480. In an embodiment, housing interface portion 480 may be electrically coupled with circuitry contained within housing 402.

Isolation connector 408 further includes insulator portion 409 disposed adjacent to housing interface portion 480. In an embodiment, insulator portion 409 is operative to insulate housing 402 from components of IID 401 disposed beyond insulator portion 409.

In another embodiment, insulator portion 409 is operative to insulating housing 402 from components 403, 404 disposed within housing 402.

In an embodiment, an RF filter (not depicted in FIG. 4) may be disposed proximal to insulator portion 409. In various embodiments, the RF filter may be operable to filter noise that may enter IID 401 at or near insulator portion 409.

In various embodiments, isolation connector 408 includes feed-through channel 440. Feed-through channel may be defined through housing interface portion 480 and insulator portion 409 such that components 403, 404 contained within housing 402 may be electrically coupled via an electrical conductor disposed in the feed-through channel 440 to components disposed beyond insulator portion 409.

In some embodiments, feed-through channel 408 is constructed to be of a much smaller diameter than a diameter of isolation connector 408. In other embodiments, feed through channel 408 is constructed to be of nearly the diameter of isolation connector 408.

In some embodiments, feed-through channel 408 may be adapted to function as a fluid reservoir or a pass through for a fluid when IID 401 is adapted to deliver drug therapy to a patient.

Figure 5:
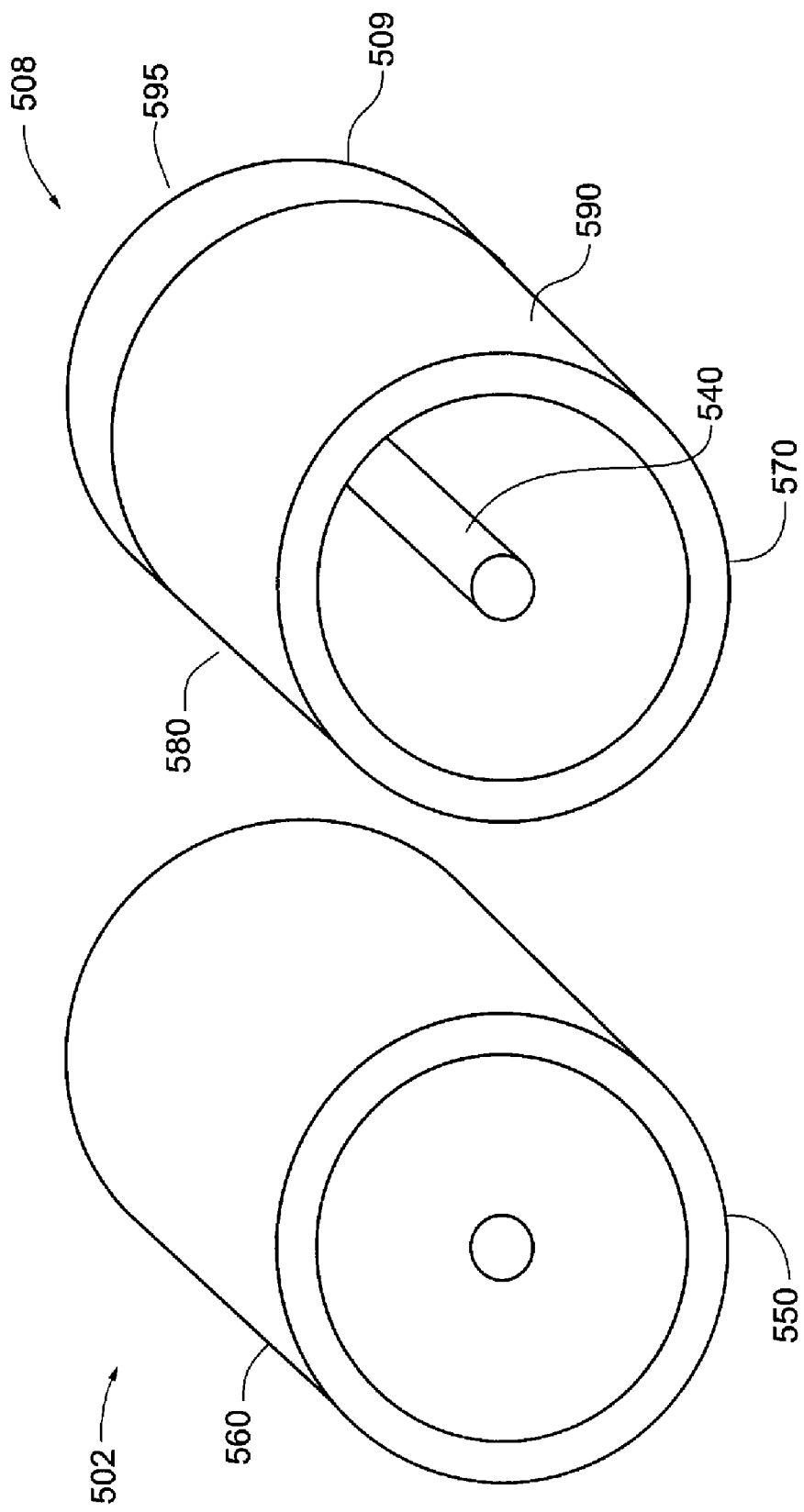
FIG. 5 illustrates generally one embodiment of an isolation connector and an IID housing according to various aspects of the invention described herein.

FIG. 5 illustrates generally one embodiment of isolation connector 508 and housing 502 according to various aspects of the invention described herein. As shown in FIG. 5, an annular perimeter 570 of housing interface portion 580 is defined by a cross-sectional dimension of annular outer surface 590. Also shown in FIG. 5, housing interface portion 580 is constructed to be obverse to first end 550 of housing 502 such the housing 502 may be coupled to isolation connector 508. In some embodiments, annular perimeter 550 of housing interface portion 580 is constructed to be of substantially similar size and shape as first end 550 of housing 502.

Figure 6:
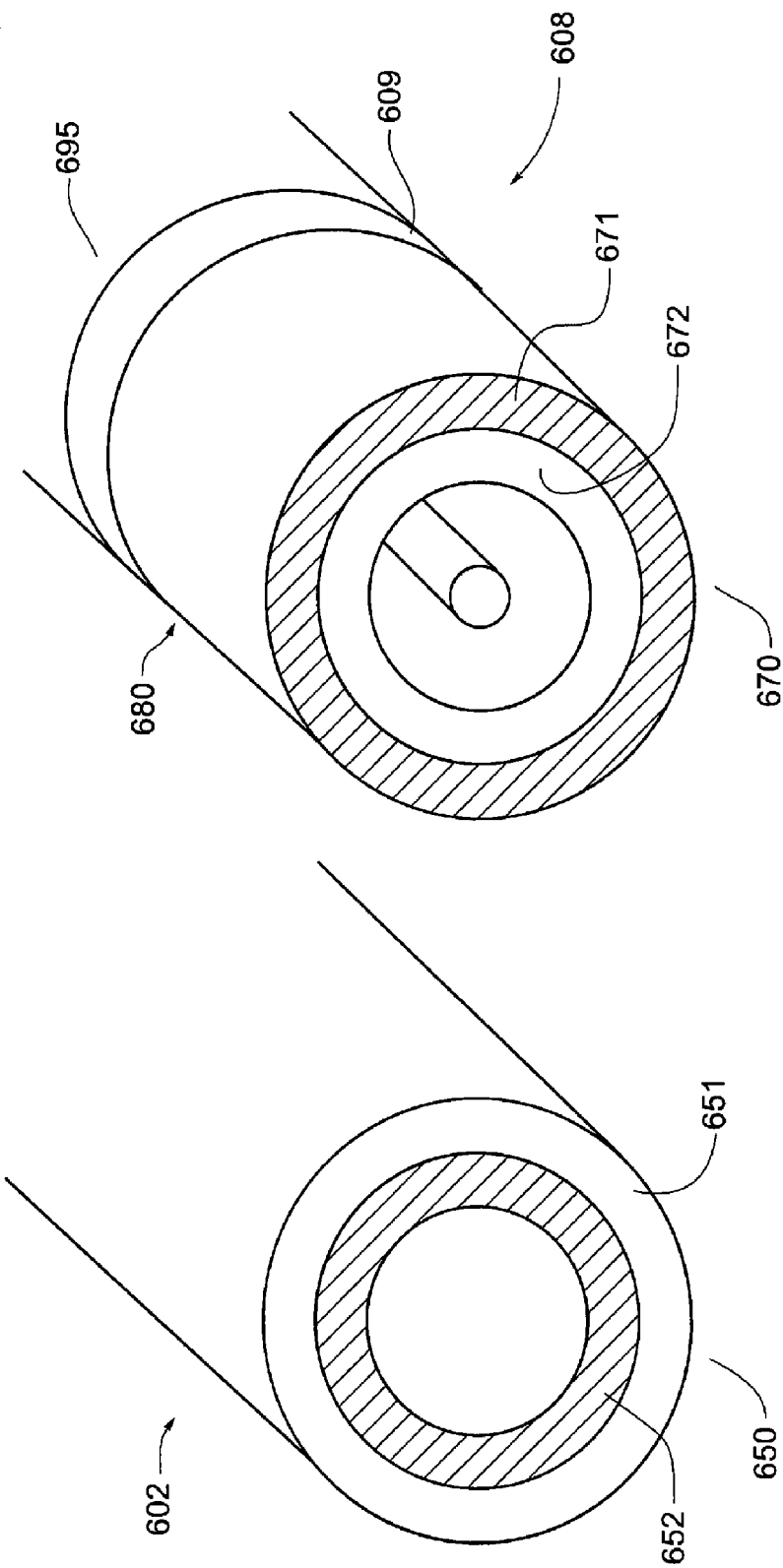
FIG. 6 illustrates generally an alternative view of one embodiment of an isolation connector and IID housing according to various aspects of the invention described herein.

FIG. 6 illustrates generally one embodiment of isolation connector 608 and IMD housing 602 according to various aspects of the invention described herein. According this embodiment, first end 650 of housing 602 includes recessed portion 652 and protruding portion 651. Housing interface portion 680 is constructed to be obverse to first end 650 of housing 630. As such, housing interface portion 680 includes end 670 that includes recessed portion 671 and protruding portion 672. According to this embodiment, protruding portion 672 is constructed to interface with recessed portion 652 of housing 630, and recessed portion 671 is constructed to interface with protruding portion 651 of housing 630.

Figure 7:
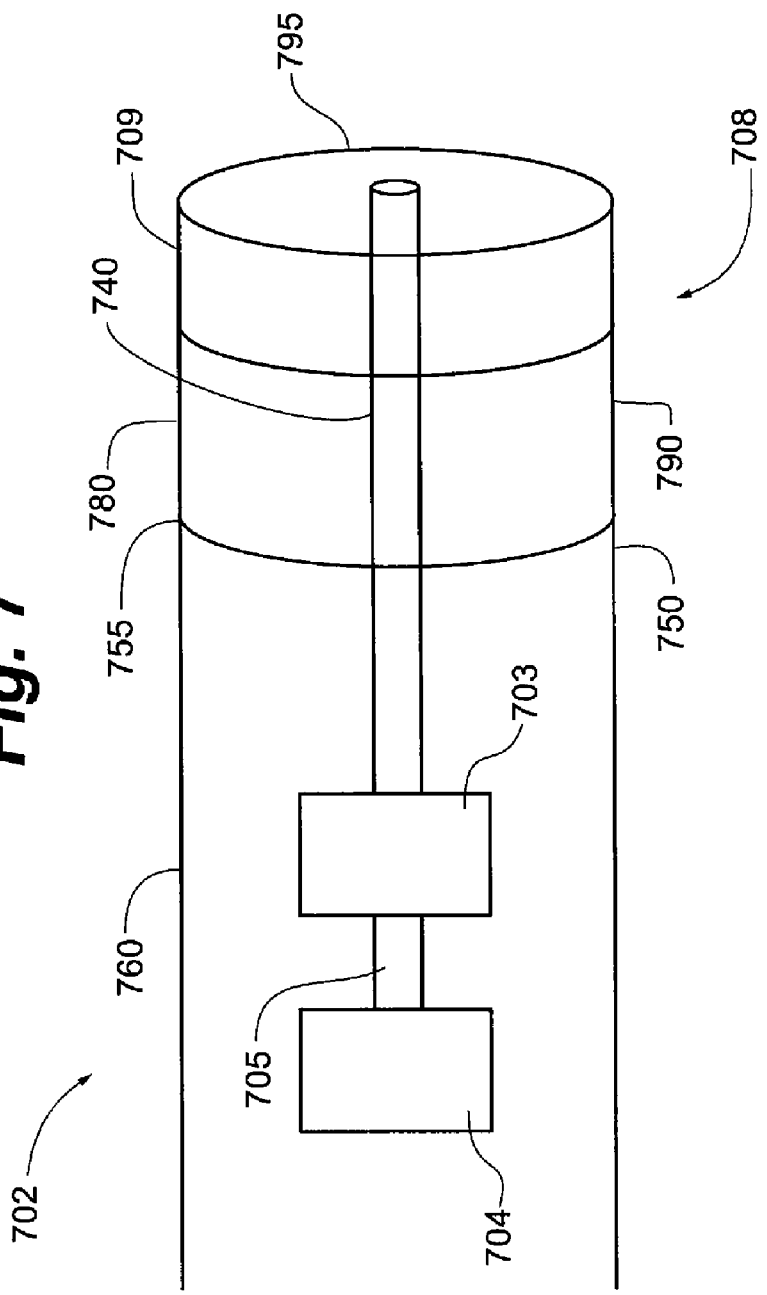
FIG. 7 illustrates generally one embodiment of an isolation connector coupled to an IID housing according to various aspects of the invention described herein.

FIG. 7 illustrates generally one embodiment of isolation connector 708 coupled to housing 702 according to various aspects of the invention described herein. As shown, first end 750 is coupled to housing interface portion 780 to define housing/isolation connector interface 755. As shown in FIG. 7, housing/isolation connector interface 755 is constructed to be substantially flush. In some embodiments, housing/isolation connector interface 755 is constructed to present a protrusion of no greater than 0.010 inches between annular surface 760 and annular surface 790. In some embodiments, housing/isolation connector interface 755 is constructed to present a protrusion of no greater than 0.0050 inches and optimally no greater than 0.0025 inches between annular surface 760 and annular surface 790. In an alternative embodiment, annular perimeter 491 of housing interface portion 480 is not of substantially similar size and shape to the annular perimeter 451 of first end 450. According to this embodiment, annular perimeter 491 may have a greater diameter than annular perimeter 451, or annular perimeter 451 may have a greater diameter than annular perimeter 491. Also according to this embodiment, the annular perimeter 451 or 491 with a greater dimension may be constructed to be generally arcuate in reference to an exterior surface of the adjacent component minimize any sharp protrusions of the interface between housing 430 and isolation connector 408.

In an embodiment, housing interface portion 780 is secured to first end 750 of housing 702 through laser welding or brazing.

In various embodiments, insulator portion 709 is also constructed to have an annular surface that defines a perimeter of a side of insulator portion 709 disposed adjacent to housing interface portion 780. In one such embodiment, an annular perimeter of insulator portion 709 is constructed to be of substantially similar size and shape as annular perimeter 790 of housing interface portion 780 so as to provide a substantially flush interface between housing interface portion 780 and insulator portion 709. In an embodiment, this interface is constructed to present a protrusion of no greater than 0.010 inches. In another embodiment, this interface is constructed to present a protrusion of no greater than 0.0050 inches and optimally no greater then 0.0025 inches.

Figure 8:
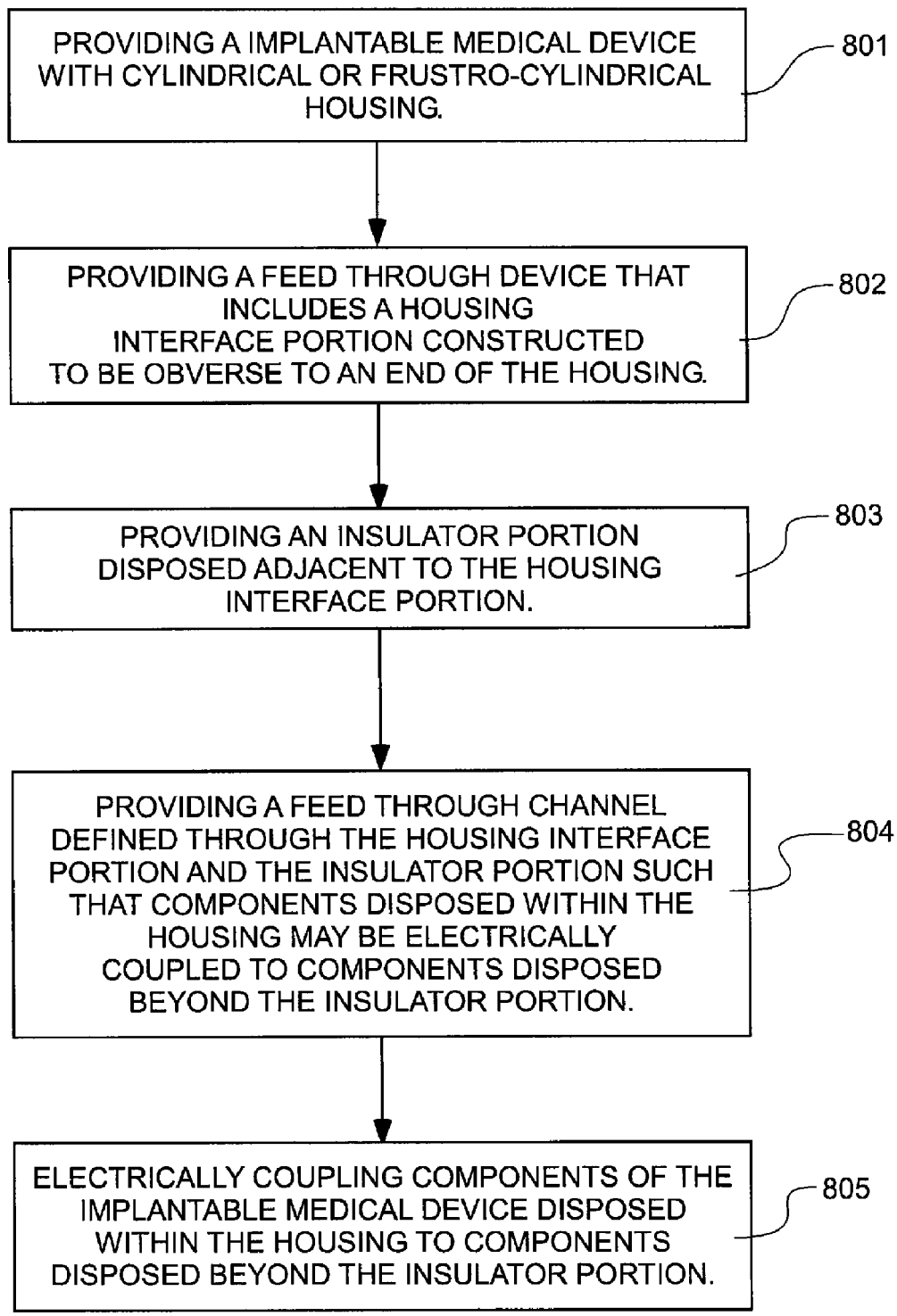
FIG. 8 illustrates generally one embodiment of a method of securing an isolation connector to a housing of an implantable medical device according to various aspects of the invention described herein.

FIG. 8 illustrates generally one embodiment of a method of securing a isolation connector to a housing of an implantable medical device according to various aspects of the invention described herein. At 801, an implantable medical device with a cylindrical or frustro-cylindrical housing is provided. In an embodiment, a substantially annular exterior surface of the housing defines a perimeter of a first end of the housing. At 802, a isolation connector is provided that includes a housing interface portion constructed to be obverse to the first end of the housing. In an embodiment, a perimeter of the housing interface portion is constructed to be of substantially similar size and shape to a perimeter of the first end of the implantable medical device housing. At 803, an insulator portion is disposed adjacent to the housing interface portion. Optionally, at 804, a feed-through channel is defined through the housing interface and the insulator portion. In an embodiment, feed-through channel is defined such that components disposed within the housing may be electrically coupled to components disposed beyond the insulator portion. In another embodiment, feed-through channel is defined to allow passage of fluid for purposes of drug delivery. At 805, the first end of the housing is secured to the interface portion of the isolation connector.

Figure 9:
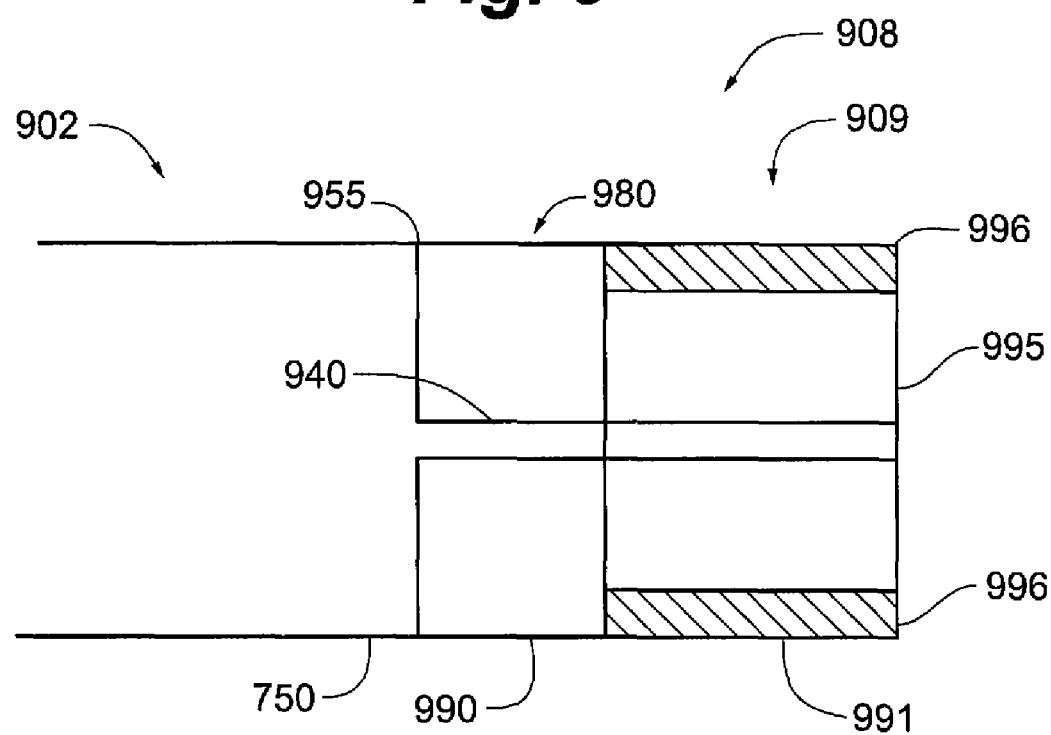
FIG. 9 illustrates generally one embodiment of an isolation connector coupled to an IID housing wherein an insulator portion of the isolation connector is coated with a hermetic material according to various aspects of the invention described herein.

FIG. 9 illustrates generally one embodiment of isolation connector 908 coupled to housing 902 according to various aspects of the invention described herein. According to the embodiment illustrated in FIG. 9, a perimeter of insulator material disposed within insulator portion 909 adjacent to housing interface portion 980 is constructed to be of smaller size than a perimeter of housing interface portion 990. According to this embodiment, insulator portion 909 is coated with a hermetic material 996 so as to define an annular exterior surface 939 of substantially similar size and shape as annular exterior surface 990 of housing interface portion 980. In an embodiment, hermetic material 996 is a polymer. In another embodiment, hermetic material 996 is a silicone. In yet another embodiment, hermetic material 996 is a polyurethane-silicone hybrid. In another embodiment, hermetic material 996 includes hydrophilic polyvinylpyrrolidone ("PVP"). In an embodiment, PVP may be applied with a tie layer. In another embodiment, PVP may be applied with a drug such as heparin.

Components of isolation connector described with respect to FIGS. 10-17 below may each in turn present a generally annular exterior surface that defines an annular perimeter of a first and second end of each component. As such, components of each isolation connector embodiment discussed below may be constructed to present first and second ends that are obverse to an annular perimeter of an adjacent component as discussed above with respect to housing interface portion 780 and insulator portion 708.

In an embodiment, components of each isolation connector embodiment discussed below may be constructed to present an annular perimeter of substantially similar diameter to an annular perimeter of an adjacent component. In an alternative embodiment, the annular perimeters of components of isolation connectors described with respect to FIGS. 10-17 below may not be of substantially similar diameter as an the annular perimeter of an adjacent component. According to these embodiments, a component with an annular perimeter of a greater diameter than an adjacent component may be constructed to be arcuate at an end obverse to the adjacent component so as to minimize any sharp protrusion relative to an exterior surface of the adjacent component.

In various embodiments, components of isolation connector such as housing interface portion 980 and insulator portion 909, and components of isolation connector as discussed below with respect to FIGS. 10-17, may be individually or in combination coated with a hermetic material. In an embodiment, the hermetic material is a polymer. In another embodiment, the hermetic material is a silicone. In yet another embodiment, the hermetic material is a polyurethane-silicone hybrid. In another embodiment, hermetic material includes hydrophilic polyvinylpyrrolidone ("PVP"). In an embodiment, PVP may be applied with a tie layer. In another embodiment, PVP may be applied with a drug such as heparin.

FIGS. 10a and 10b illustrate generally embodiments of isolation connector 1008 coupled to housing 1002 according to various aspects of the invention described herein. These embodiments are similar to the embodiment illustrated in FIG. 7, except isolation connector 1008 further includes second interface portion 1091. Second interface portion 1091 is positioned adjacent to insulator portion 1009.

FIG. 10a illustrates generally one embodiment of isolation connector 1008 with second interface portion 1081 at distal end 1095 coupled to a proximal end 1026 of a bellows 1025. As shown, feed-through channel 1040 is defined through housing interface portion 1080, insulator portion 1009, and second interface portion 1081. In various embodiments, feed-through channel 1040 is constructed such that an electrical conductor disposed within feed-through channel 1040 may electrically couple components disposed within housing 1002 to components disposed beyond second interface portion 1080. In one embodiment, feed-through channel 1040 may be utilized to couple components disposed within housing 1002 to components disposed within bellows 1025. In another embodiment, feed-through channel 1040 may be utilized to couple components disposed within housing 1002 to components disposed within a second housing (not shown) coupled to a distal end 927 of bellows.

FIG. 10b illustrates generally one embodiment of isolation connector 1008 with second interface portion 1081 at distal end 1095 coupled to second IMD housing 1035. In various embodiments, feed-through channel 1040 is constructed such that an electrical conductor disposed within feed-through channel 1040 may electrically couple components disposed within first housing 1002 to components disposed within second housing 1035.

In an embodiment related to those illustrated in FIG. 10b, feed-through channel 1040 may not be adapted to electrically coupled components disposed within first housing to components disposed beyond isolation connector 1008. Instead, feed-through channel 1040 may be constructed to be a fluid reservoir or fluid conduit to facilitate delivery of drug therapy. Accordingly feed-through channel 1040 may not be of a narrow diameter relative to a diameter of isolation connector 1008. In this embodiment, the feed-through channel may be a hollow interior across housing interface portion 1080, insulator portion 1009, and second interface portion 1081.

In another embodiment, isolation connector 1008 may not include insulator portion 1009. According to this embodiment, housing interface portion 1080 and second interface portion 1081 may be constructed to be obverse to one another. In one such embodiment, housing interface portion 1080 and second interface portion 1081 may be constructed of an insulating material such as a ceramic. In another such embodiment, an exterior of housing interface portion 1080 and second interface portion 1081 may be constructed of a metal or other material, and an interior of housing interface portion 1080 and second interface portion 1081 may be filled with an insulative material.

In another embodiment, isolation connector 1008 may not be adapted to electrically connect components of an IID contained within housing 1060 to components disposed beyond isolation connector 1008 or isolation connector may not be adapted to function as a fluid reservoir or fluid pass through. According to these embodiments, isolation connector 1008 may be adapted to function as a buffer between an IID component (such as housing 1060) and other IID components, or the environment in which IID 1060 is disposed within a patient. According to these embodiments, isolation connector may be filled with a solid material, formed of a single material, or include a hollow space within isolation connector.

Figure 11:
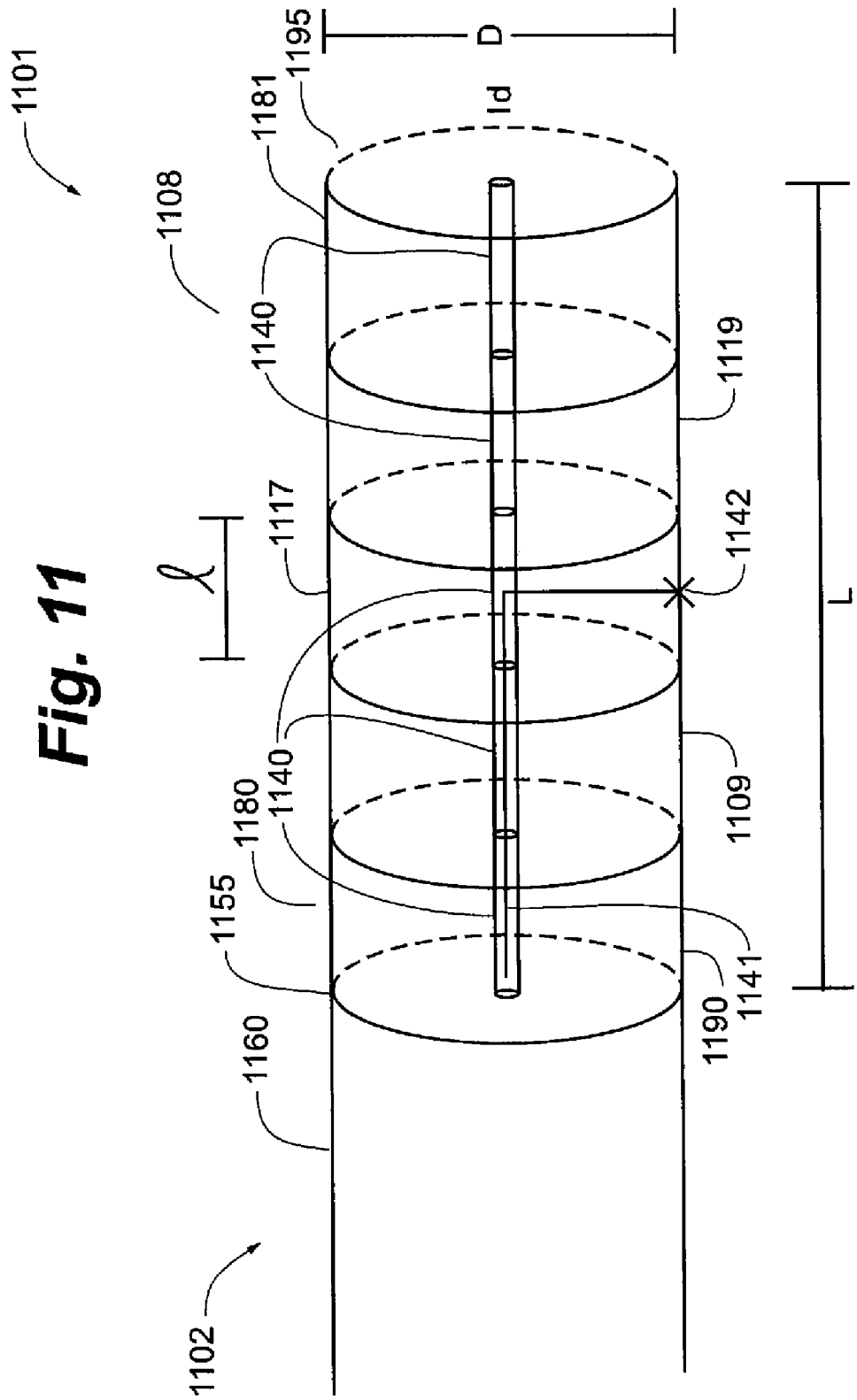
FIG. 11 illustrates generally one embodiment of an isolation connector that includes a conductive portion according to various aspects of the invention described herein.

FIG. 11 illustrates generally one embodiment of isolation connector 1108 that includes a conductive portion 1117 according to various aspects of the invention described herein. Conductive portion 1117 is disposed adjacent to first insulator portion 1109. The isolation connector 1108 embodiment illustrated in FIG. 11 further includes second insulator portion 1119. As shown, second insulator portion 1119 is positioned adjacent a distal end of conductive portion 1117. A proximal end of second insulator portion 1119 may be constructed to be obverse to a distal end of conductor portion 1117.

Isolation connector 1108 may further include second interface portion 1081 positioned adjacent to second insulator portion 1119. A proximal end of second interface portion 1081 may be constructed to be obverse to a distal end of conductive portion 1117.

FIG. 11 also shows feed-through channel 1140. In various embodiments, feed-through channel 1140 defined through housing interface portion 1180, first insulator portion 1109, conductive portion 1117, second insulator portion 1119, and second interface portion 1181. In various embodiments, one or more electrical conductors 1141 may be disposed within feed-through channel 1140.

In one embodiment, electrical conductor 1141 disposed within feed-through channel 1140 may be electrically coupled to conductive portion 1117. In an embodiment, conductive portion 1117 is constructed to present a conductive outer surface 1142. As such, conductive portion 1117 may be electrically coupled to components disposed within housing 1102 and is operative to function as an electrode of IID 1101.

Electrical circuitry disposed within housing may be adapted to control the disposition of electrical energy or the sensing of hemodynamic conditions by utilizing conductive portion 1117 as an electrode of IID 1101. In another embodiment, conductive portion 1117 may be adapted to be coupled to components of IID 1101 disposed beyond distal end of isolation connector 1108, such as in an additional housing. According to this embodiment, electrical circuitry disposed beyond second insulator portion 1119 may be adapted to control the disposition of electrical energy or the sensing of hemodynamic conditions by utilizing conductive portion 1117 as an electrode of IID 1101.

According to the embodiment of isolation connector 1108 depicted in FIG. 11, first insulator portion 1109 is operative to electrically insulate conductive portion 1117 from housing 1102 of IID 1101. Second insulator portion 1119 may be operative to electrically insulate conductive portion 1117 from components of IID 1101 not disposed within housing 1102, such as a second housing, a bellows, or one or more leads (not depicted in FIG. 11).

Figure 12:
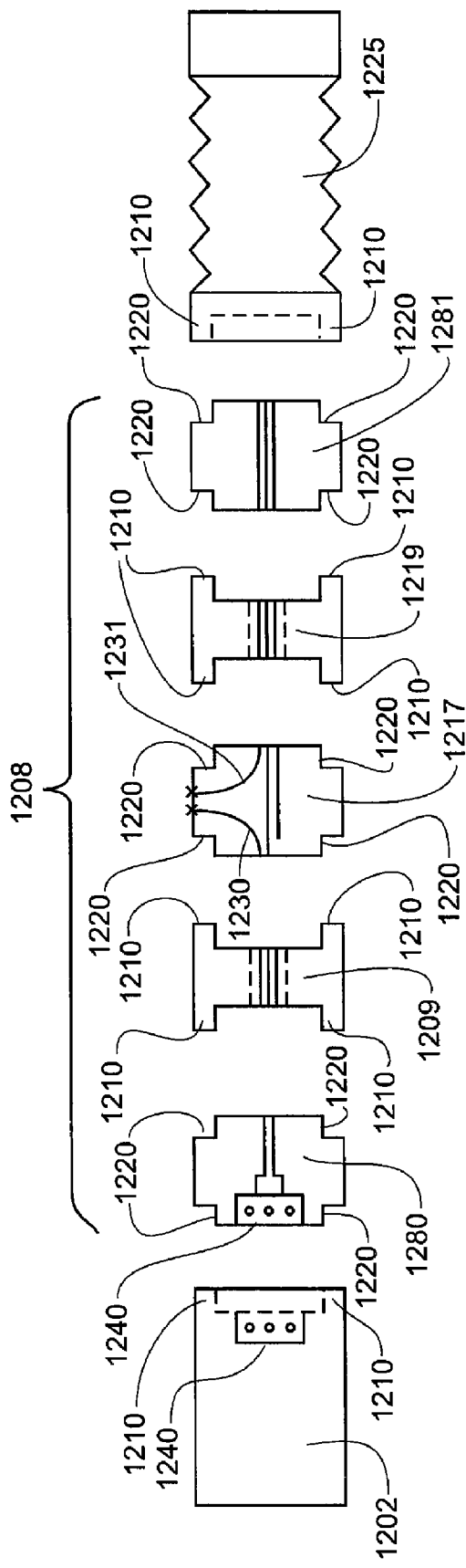
FIG. 12 illustrates generally an exploded side view of one embodiment of an isolation connector according to various aspects of the invention described herein.

FIG. 12 illustrates generally an exploded side view of one embodiment of a isolation connector 1208 according to various aspects of the invention described herein. FIG. 12 shows various isolation connector 1208 components including housing interface portion 1280, first insulator portion 1209, conductive portion 1117, second insulator portion 1219, and second interface portion 1281. As illustrated, an end of each component may be constructed to present a mating interface with an end of an adjacent portion. In an embodiment, this mating interface portion may be a flange 1210 or other protrusion constructed to interface with an associated recessed portion 1220. Although FIG. 12 illustrates certain components with flange portions 1210 or recessed portions 1220, these mating interfaces are interchangeable between different components of isolation connector 1208.

Also illustrated in FIG. 12, at adjacent ends of housing 1202 and housing interface portion 1280, are electrical couplers 1240. Electrical couplers 1240 may provide an electrical connection between one or more electrical conductors disposed within housing 1202, bellows 1225, or components of isolation connector 1208. Although electrical couplers 1240 are shown at an interface between housing 1202 and housing interface portion 1280, any components of isolation connector 1208 may include electrical couplers 1240.

The isolation connector of FIG. 12 also includes electrical conductors 1230 and 1231. Electrical conductor 1230 includes a first end coupled with electrical circuitry contained within housing 1202, while electrical conductor 1231 includes a first end coupled to components disposed within or beyond bellows 1225. A second end of electrical couplers 1230 1231 is electrically coupled with an exterior surface of conductor portion 1117. As such, conductive portion may be operable to function as an electrode of implantable medical device 1201.

In an embodiment, isolation connector 1108 is constructed to have a length L as depicted in FIG. 11. In an embodiment, L is between about 5.0 mm and 10.0 mm. In another embodiment, L is about 7.0 mm. In an embodiment, conductive portion 1117 of isolation connector 1108 is constructed to have a length l as depicted in FIG. 11. In an embodiment, l has a length of between about 0.5 mm and 4.0 mm. In another embodiment, l is about 2.0 mm. In various embodiments, the length of components of isolation connector 1180, 1109, 1117, 1119, and 1181 may each be adjusted to create any desire length L of isolation connector 1108.

In various embodiments, isolation connector 1108 has an outer diameter D. In an embodiment, D is between about 5.0 mm and about 10.0 mm. In another embodiment, D is about 7.0 mm. In various embodiments, isolation connector includes feed-through channel 1140 with a diameter d as depicted in FIG. 11. In an embodiment, d is between about 1.0 and about 5.0 mm. In another embodiment, d is about 3.0 mm.

Those skilled in the art will recognize that any number of conductive portions and insulator portions can be included in isolation connector 1102. For example, while the isolation connector 1102 depicted in FIG. 11 includes one conductor portion 1117, any number of conductive members is contemplated by the present disclosure. Also, for example, while the isolation connector 1102 depicted in FIG. 11 includes two insulative members 1109, 1119, any number of insulative members is contemplated by the present disclosure.

FIG. 13 illustrates generally one embodiment of a method of providing a isolation connector for an IMD housing according to various aspects of the invention described herein. At 1301, an implantable intravascular medical device is provided that includes a cylindrical or frustro-cylindrical housing. In an embodiment, a substantially annular exterior surface of the housing defines a perimeter of a first end of the housing. At 1302, a housing interface is coupled to the housing. The housing interface portion is constructed to be obverse to a first end of the housing. In an embodiment, a perimeter of the housing interface portion is constructed to be of substantially similar size and shape to a perimeter of the first end of the housing. At 1303, a first insulator portion is disposed adjacent to the housing interface portion. In an embodiment, a generally annular perimeter of the first insulator portion is of substantially similar size and shape to the annular perimeter of the housing interface portion. At 1304, a conductive portion is disposed adjacent to the first insulator portion. In an embodiment, a generally annular perimeter of the first insulator portion is of substantially similar size and shape to the annular perimeter of the housing interface portion. At 1305, a second insulator portion is disposed adjacent to the conductive portion. In an embodiment, a generally annular perimeter of the second insulator portion is of substantially similar size and shape to the annular perimeter of the conductive portion. At 1306, a second interface portion is disposed adjacent to the second insulator portion. In an embodiment, a generally annular perimeter of the second interface portion is of substantially similar size and shape to the annular perimeter of the conductive portion. At 1306, a feed-through channel is defined between the housing interface portion, the first insulator portion, the conductive portion, the second insulator portion, and the second interface portion. In one embodiment, at 1307, components disposed within the housing are electrically coupled with the conductive portion. In another embodiment, at 1308, components disposed beyond the second interface portion are electrically coupled to the conductive portion. In yet another embodiment, at 1309, components disposed within the housing are electrically coupled to components disposed beyond the second interface portion.

FIG. 14 illustrates generally a flattened perspective view of isolation connector 10. Isolation connector 10 includes a housing interface portion 16a coupled to housing 20, a first insulator portion 14a coupled to housing interface portion 16a, conductor portion 12 coupled to first insulator portion 14a, second insulator portion 22 coupled to conductor portion 12, and second interface portion 16b coupled to second insulator portion 14b. Second interface portion 16b is shown coupled to bellows 18. As depicted in FIG. 14, isolation connector 10 includes feed-through channel 22. As shown, feed-through channel is defined through first and second insulator portions 14a, 14b and is of a much smaller diameter d than a diameter of isolation connector 10. Also shown, feed-through channel 22 is not of a diameter d through housing interface portion 16a, conductor portion 12, and second interface portion 16b. Instead, feed-through channel 22 defined through these components is merely a hollow cavity in the respective component.

FIG. 15 illustrates generally an flattened perspective view of isolation connector 110. As shown, a proximal end of isolation connector 10 is coupled to a first IID housing 120. A distal end of isolation connector 10 is coupled to a proximal end of bellows 118, while a distal end of bellows 118 is coupled to second IID housing 120'.

FIG. 16 illustrates generally a flattened perspective view of a isolation connector 210 that include first, second and third insulator portions 214a, 214b, and 214c, respectively. Isolation connector 210 also include a first conductor portion 212a disposed between first and second insulator portions 214a, 214b. Second conductor portion 212b is disposed between second and third insulator portions 214b and 214c.

Figure 17A:
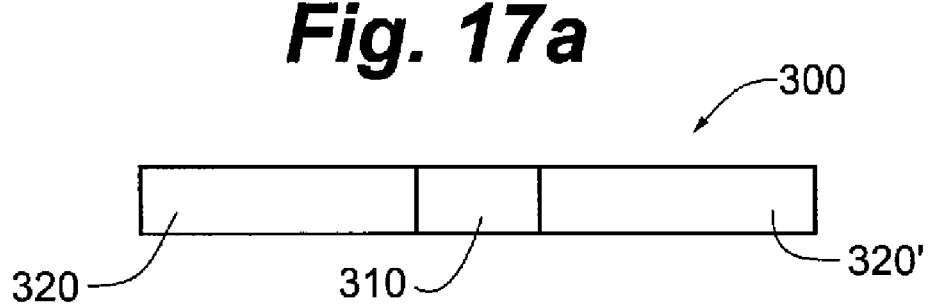
FIGS. 17a-b illustrate generally embodiments of an isolation connector according to various aspects of the invention described herein.
Figure 17B:
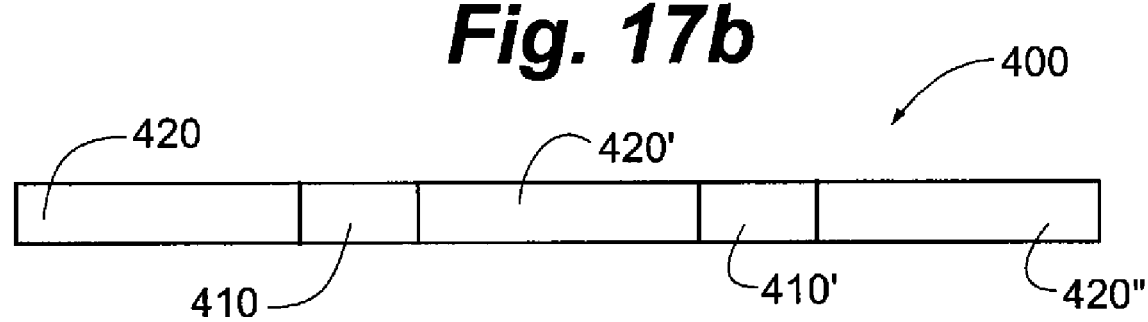

FIGS. 17a-b illustrate generally various embodiments of an isolation connector according to various aspects of the invention described herein. FIG. 17a illustrates isolation connector 300 which includes first interface portion 320 and second interface portion 320'. Insulator portion 310 is disposed between first interface portion 320 and second interface portion 320'. FIG. 17b illustrates isolation connector 400 which includes first interface portion 420 and second interface portion 420". Disposed between first interface portion 420 and second interface portion 420" is first insulator portion 410, conductor portion 420', and second insulator portion 410'.

Finally, while the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

What is claimed is:

1. An implantable intravascular medical device, comprising:
    a generally cylindrical or frustro-cylindrical implantable intravascular medical device housing operable to contain at least one electronic component wholly within said housing and constructed to present a generally annular exterior surface and a first end with a perimeter defined by a cross-section of said exterior surface;
    an isolation connector with a generally annular exterior surface that includes a proximal end and a distal end;
    a housing interface portion at a proximal end of said isolation connector secured to said housing, wherein said housing interface portion includes a proximal end obverse to said first end of said housing, said proximal end constructed to present a perimeter of substantially similar size and shape to said perimeter of said first end of said housing;
    a first insulator portion disposed adjacent to a distal end of said housing interface portion; and
    a feed-through channel constructed to traverse said proximal end and said distal end and defined through said housing interface portion and said first insulator portion.

2. The device of claim 1, further comprising:
    an electrical conductor disposed within said channel so as to electrically couple said at least one component disposed within said housing to at least component disposed beyond said insulator portion.

3. The device of claim 1, wherein said feed-through channel is constructed to function as a fluid reservoir or fluid pass through.

4. The device of claim 1, wherein said first insulator portion is operative to electrically insulate said electrical conductor from said housing.

5. The device of claim 1, wherein said isolation connector is constructed such that said generally annular exterior surface of said housing is generally flush with said generally annular exterior surface of said isolation connector.

6. The device of claim 1, wherein an interface between said housing and said housing interface portion is constructed to present a protrusion of no greater than 0.010 inches with respect to said generally annular surface of said housing.

7. The device of claim 1, further comprising:
    a conductor portion disposed adjacent said first insulator portion.

8. The device of claim 7, wherein said first insulator portion is operative to insulate said conductor portion from said housing.

9. The device of claim 7, wherein said electrical conductor disposed within said channel is adapted to electrically couple circuitry disposed within said housing to said conductor portion.

10. The device of claim 7, further comprising:
    a second insulator portion disposed adjacent to said conductor portion; and
    a second interface portion disposed adjacent to said second insulator portion.

11. The device of claim 10, wherein said feed-through channel is defined through said housing interface portion, said first insulator portion, said conductor portion, said second insulator portion, and said second interface portion.

12. The device of claim 10, wherein said second insulator portion is operative to electrically isolate said conductor from components disposed beyond a distal end of said isolation connector.

13. The device of claim 10, wherein said housing interface portion, said first insulator portion, said conductor portion, said second insulator portion, and said second interface portion are each constructed to define a generally annular and generally continuous exterior surface of substantially similar cross-dimensional size and shape to said cross-dimension of said annular exterior surface of said housing.

14. A method of electrically coupling a first component of an intravascular implantable medical device disposed within a generally cylindrical cylindrical housing to a second component of said implantable intravascular medical device not disposed within said housing, comprising:
    coupling a housing interface portion constructed to present an annular coupling end of substantially similar size and shape to at least one end of said housing;
    coupling a first insulator portion to a distal end of said housing interface portion; and
    electrically coupling said first component of said intravascular implantable medical device to said second component of said intravascular implantable medical device via an electrical conductor at least partially disposed within a feed-through channel defined through said housing interface portion and said insulator portion.

15. The method of claim 4, further comprising:
    coupling a conductive portion at a distal end of said insulator portion, wherein said insulator portion is operative to electrically isolate said conductive portion from said housing; and
    electrically coupling, via said electrical conductor, said at least one component of said implantable intravascular medical device to said conductor portion.

16. The method of claim 14, further comprising:
    coupling a second insulator portion to said conductive portion, wherein said second insulator portion is operative to electrically isolate said conductive portion from components of implantable intravascular medical device disposed beyond said insulator portion; and coupling a second interface portion to said second insulator portion.

17. The method of claim 16, further comprising:
coupling a distal end of said second interface to a component of said implantable medical device selected from the group consisting of:

a second implantable intravascular medical device housing;
a lead; and
a flexible member.

* * * * *